(12) United States Patent
Nguyen et al.

(10) Patent No.: US 7,497,215 B1
(45) Date of Patent: Mar. 3, 2009

(54) MEDICAL VENTILATOR WITH COMPRESSOR HEATED EXHALATION FILTER

(75) Inventors: Patrick Nguyen, Carlsbad, CA (US); Gardner J. Kimm, Carlsbad, CA (US); Steve Han, Upland, CA (US); Mabini M. Arcilla, San Diego, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 366 days.

(21) Appl. No.: 10/742,382

(22) Filed: Dec. 19, 2003

Related U.S. Application Data

(60) Provisional application No. 60/435,112, filed on Dec. 20, 2002.

(51) Int. Cl.
| | |
|---|---|
| A61M 16/00 | (2006.01) |
| A62B 7/00 | (2006.01) |
| A62B 7/10 | (2006.01) |
| A62B 23/02 | (2006.01) |
| F24J 3/00 | (2006.01) |
| F16K 31/02 | (2006.01) |

(52) U.S. Cl. .................. 128/204.17; 128/204.21; 128/205.27; 128/205.29

(58) Field of Classification Search ........... 128/204.17, 128/204.18, 204.21, 204.23, 204.25, 205.12, 128/205.18, 205.27–28, 200.24, 205.29
See application file for complete search history.

(56) References Cited

U.S. PATENT DOCUMENTS

| | | | | |
|---|---|---|---|---|
| 3,807,396 | A * | 4/1974 | Fischel | 128/201.21 |
| 3,921,002 | A * | 11/1975 | Williams et al. | 422/186.11 |
| 4,480,956 | A * | 11/1984 | Kruger et al. | 416/97 A |
| 4,482,091 | A * | 11/1984 | Lawsing | 236/92 R |
| 4,727,871 | A | 3/1988 | Smargiassi et al. | |
| 5,452,714 | A | 9/1995 | Anderson et al. | |
| 5,868,133 | A | 2/1999 | DeVries et al. | |
| 5,954,051 | A | 9/1999 | Heinonen et al. | |
| 6,782,888 | B1 * | 8/2004 | Friberg et al. | 128/204.18 |
| 2002/0053345 | A1 * | 5/2002 | Jafari et al. | 128/204.23 |
| 2003/0029453 | A1 * | 2/2003 | Smith et al. | 128/204.23 |
| 2005/0072426 | A1 * | 4/2005 | Deane et al. | 128/204.26 |

* cited by examiner

*Primary Examiner*—Justine R Yu
*Assistant Examiner*—Kristen C Matter
(74) *Attorney, Agent, or Firm*—Michael W. Haas

(57) ABSTRACT

A medical ventilator includes a pressure generator for increasing a pressure of gas that produces heat during the operation thereof. A heat sink spaced from the pressure generator is provided for absorbing heat from the pressure generator. A bacteria filter requiring heating in excess of an ambient temperature for the effective operation thereof is coupled in thermal communication with the heat sink. A heat pipe is coupled in thermal communication with the heat sink and the pressure generator for conveying at least part of heat produced by the pressure generator to the bacteria filter via the heat sink.

16 Claims, 3 Drawing Sheets

MEDICAL VENTILATOR WITH COMPRESSOR HEATED EXHALATION FILTER

CROSS-REFERENCE TO RELATED APPLICATIONS

This application claims priority under 35 U.S.C. § 119(e) from provisional U.S. patent application No. 60/435,112 filed Dec. 20, 2002 the contents of which are incorporated herein by reference.

BACKGROUND OF THE INVENTION

1. Field of the Invention

The present invention pertains to a medical ventilator and, more particularly, to redistributing heat produced during operation of the medical ventilator.

2. Description of Related Art

Heretofore, medical ventilators included a pressure generator encapsulated in a suitable noise suppression material, such as foam, to muffle noise produced by the pressure generator during operation. While encapsulating the pressure generator in foam has the desired effect of muffling noise produced by the pressure generator, the foam also acts as an insulator that traps in the pressure generator heat produced thereby during operation. Because the pressure generator is utilized to increase the pressure of gas provided to a patient, the heat trapped in the pressure generator undesirably increases the temperature of the pressurized gas provided to the patient. Moreover, the trapped heat increases the operating temperature of the pressure generator thereby decreasing its efficiency.

Medical ventilators often include a bacteria filter for capturing bacteria exhaled by a patient using the medical ventilator. For effective operation, the bacteria filter requires heating in excess of ambient temperature. Heretofore, heating of the bacteria filter was accomplished by a resistive heating element placed in close proximity to the bacteria filter. This resistive heating element receives power during operation of the medical ventilator and converts the power into heat, which is transferred to the bacteria filter to increase its temperature to an effective operating temperature range. A suitable temperature control system can also be provided for monitoring the temperature of the bacteria filter and for controlling the application of electrical power to the resistive heating element in order to maintain the operating temperature of the bacteria filter in its effective operating temperature range.

While useful for heating a bacteria filter to its effective, or optimal, operating temperature range, the resistive heating element increases the temperature of the bacteria filter at the expense of the use of additional power by the medical ventilator. However, if an alternative source of heat were available, it would be desirable to either eliminate the resistive heating element as part of the medical ventilator or reduce the use of the resistive heating element for heating the bacteria filter.

SUMMARY OF THE INVENTION

It is, therefore, desirable to overcome the above problems and others by providing a method and apparatus for medical ventilation whereupon heat produced by the pressure generator is transferred therefrom to a remote position for dissipation. It is also desirable to provide an apparatus and method for medical ventilation whereupon heat produced by the pressure generator is transferred to a remotely positioned bacteria filter for heating the filter to its effective operating temperature range. Still other desirable features will become apparent to those of ordinary skill in the art upon reading and understanding the following detailed description.

The present invention is a medical ventilator that includes a patient circuit having an inspiration branch and an expiration branch. A pressure generator increases a pressure of gas to be delivered to a patient via the inspiration branch of the patient circuit. The pressure generator produces heat during its operation. The ventilator includes a device, system, or component that requires heating in excess of an ambient temperature for the effective operation of that device. This device requiring heat is spaced from the pressure generator. Lastly, a thermal conductor is coupled in thermal communication with heating requiring device and the pressure generator for transferring at least part of the heat produced by the pressure generator during its operation to device to be heated.

The ventilator can include a thermally conductive heat sink coupled in thermal communication between the heat requiring device and the thermal conductor. A fan or other device can also be provided for causing air to flow across the heat sink.

The device requiring heat can include a bacteria filter disposed in the expiration branch of the patient circuit for capturing bacteria received in the expiration branch from the patient. The thermal conductor can be a heat pipe.

The pressure generator can include a motor for driving a compressor. The compressor can be one of a blower, a piston, a bellows, a helical compressor, a drag compressor, or any other conventional device for elevating a flow of gas above ambient pressure.

The ventilator can further include an enclosure encasing the pressure generator and at least part of the thermal conductor. Insulating material can be disposed in the enclosure surrounding at least part of the pressure generator and at least part of the thermal conductor.

The invention is also a medical ventilator that includes a patient circuit having an inspiration branch and an expiration branch and a pressure generator for increasing a pressure of a gas to be delivered to a patient via the inspiration branch of the patient circuit. The pressure generator produces heat during its operation. A thermally conductive heat sink is spaced from the pressure generator and a thermal conductor is coupled in thermal communication with the pressure generator and the heat sink for transferring at least part of the heat produced by the pressure generator during the operation thereof to the heat sink.

The ventilator can include a device, system, or component requiring heating in excess of an ambient temperature for the effective operation thereof. The heat requiring can be coupled to the heat sink for receiving heat from the pressure generator via the thermal conductor and the heat sink. The heat requiring device can include a bacteria filter disposed in the expiration branch of the patient circuit for capturing bacteria received in the expiration branch from the patient.

The ventilator can include a fan or other means for forcing air to flow across the heat sink to remove at least part of the heat conducted to the heat sink by the thermal conductor. The thermal conductor can be a heat pipe. The pressure generator can include a motor for driving a compressor.

The invention is also a method of heating a component of a medical ventilator. The method includes providing a pressure generator for increasing a pressure of gas to be delivered to a patient and providing a component spaced from the pressure generator requiring heating in excess of an ambient temperature for the effective operation of that component. Heat is produced in response to operation of the pressure generator and a thermal conductor is coupled in thermal communication between the pressure generator and the component for transferring at least part of the heat produced by the pressure generator to the component.

The method can also include coupling a thermally conductive heat sink in thermal communication between the thermal conductor and the component for transferring heat from the thermal conductor to the component. The thermal conductor can be a heat pipe and the component can be a bacteria filter.

The invention is also a method of heat transfer in a medical ventilator. The method includes providing a pressure generator for increasing a pressure of gas to be delivered to a patient and providing a thermally conductive heat sink spaced from the pressure generator. Heat is produced in response to operation of the pressure generator and a thermal conductor is coupled in thermal communication between the pressure generator and the heat sink for transferring at least part of the heat produced by the pressure generator to the heat sink.

The method can also include coupling to the heat sink a component requiring heating in excess of an ambient temperature for the effective operation thereof whereupon the component receives heat from the thermal conductor via the heat sink.

Lastly, the invention is a medical ventilator that includes means for increasing a pressure of gas that produces heat during the operation thereof; means for absorbing heat spaced from the gas pressure increasing means; means requiring heating in excess of an ambient temperature for the effective operation thereof, with heat requiring means coupled in thermal communication with the absorbing means; and means coupled in thermal communication with the heat absorbing means and the pressure increasing means for conveying at least part of the heat produced by the pressure increasing means to the heat requiring means via the heat absorbing means.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
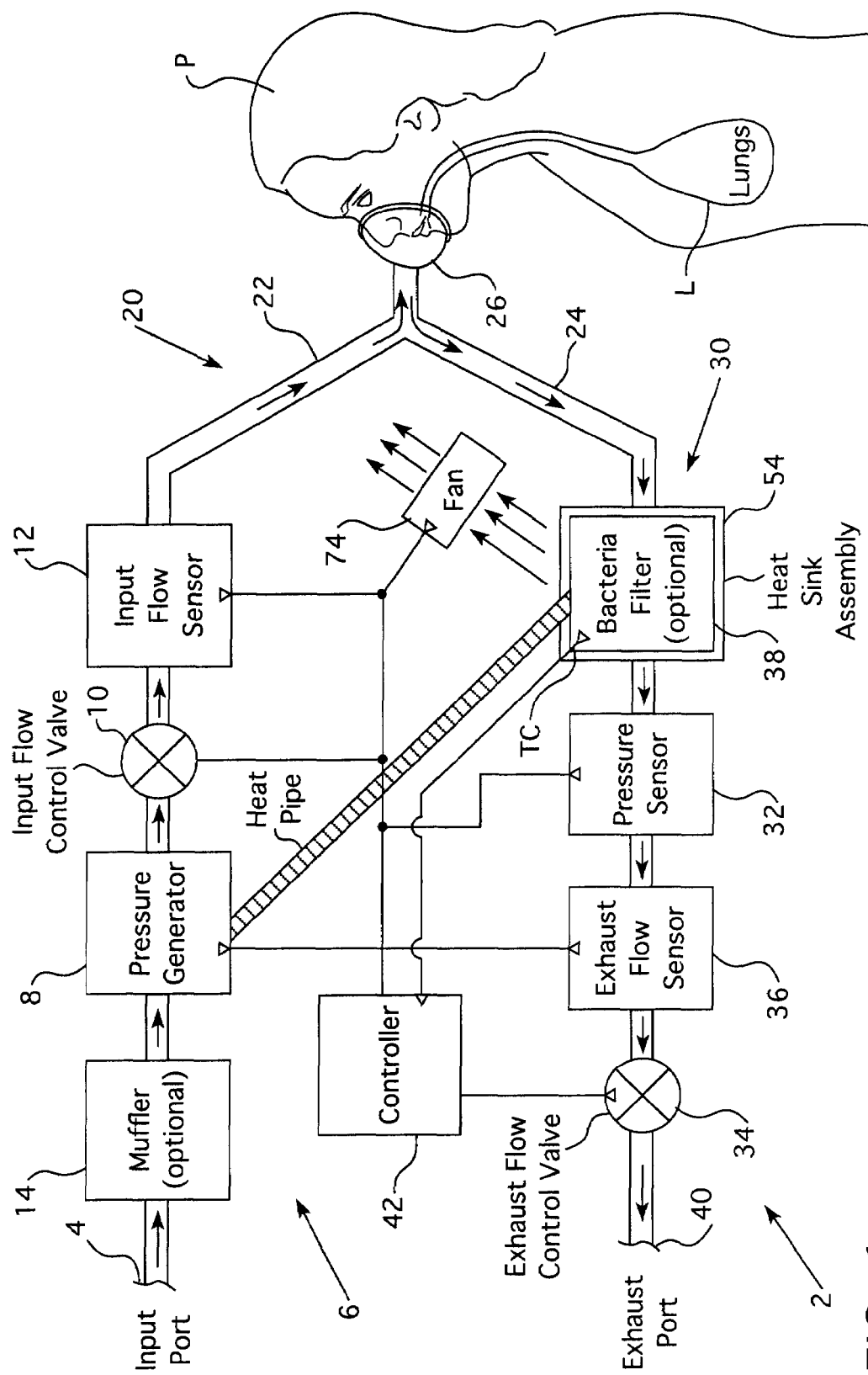
FIG. 1 is a block diagram of a medical ventilator in accordance with the present invention.

With reference to FIG. 1, a medical ventilator 2 includes an input port 4 for receiving a breathing gas, such as atmospheric air or any other suitable gas, for use by a patient P. Gas is drawn into input port 4 via a gas flow delivery system 6 that includes a pressure generator 8, an input flow control valve 10 and an input flow sensor 12. Optionally, gas flow delivery system 6 can include a muffler 14.

Pressure generator 8 is operative to elevate the pressure of the breathing gas received via input port 4. This pressurized breathing gas is provided to input flow control valve 10, which is operative to control a pressure or flow of pressurized breathing gas delivered to patient P. Input flow sensor 12 is operative for measuring the amount of fluid flowing therethrough and outputting a flow signal indicative thereof.

Gas flow delivery system 6 shows one desirable arrangement of pressure generator 8, input flow control valve 10, input flow sensor 12 and muffler 14. However, this arrangement is not to be construed as limiting the invention because other suitable arrangements of these and other components (not shown) are envisioned. For example, a flow of supplement gas, such as concentrated oxygen can in added to gas flow delivery system 6. In addition, a humidifier, pressure sensors, check valves and other components can be added to the gas f system as known in the art.

Pressurized air exiting input flow sensor 12 is delivered to a patient circuit 20 that includes an inspiration branch 22 and an expiration branch 24 coupled to a patient interface 26, such as a nasal mask, nasal/oral mask, full-face mask, tracheal tube, endotracheal tube and a nasal pillow.

When properly fitted, patient interface 26 enables pressurized gas received in inspiration branch 22 to be delivered to the lungs L of patient P via patient interface 26. Patient interface 26 also enables gas expelled from lungs L of patient P to be delivered to expiration branch 24 for delivery to a gas flow exhaust system 30.

Gas flow exhaust system 30 includes a pressure sensor 32 which is operative to measure the pressure of the exhausted gas in expiration branch 24 and to output a pressure signal corresponding thereto. This pressure signal is considered to correspond to the pressure of the exhaust gas at patient P. This pressure can also be measured directly via a pressure port (not shown) in patient interface 26.

Gas flow exhaust system 30 also includes an exhaust flow control valve 34 and an exhaust flow sensor 36, which are operative in the same manner as input flow control valve 10 and input flow sensor 12, respectively, described above. Optionally, gas flow exhaust system 30 can include a bacteria filter 38 that is operative when heated to a suitable operating temperature for capturing bacteria contained in the exhaled gas received from patient P via expiration branch 24. When bacteria filter 38 is provided, a thermocouple TC can be coupled thereto for measuring a temperature thereof. Exhaust gas passing through gas flow exhaust system 30 exits to ambient atmosphere via an exhaust port 40.

Gas flow exhaust system 30 shows one desirable arrangement of pressure sensor 32, exhaust flow control valve 34, exhaust flow sensor 36 and, if provided, bacteria filter 38. However, this arrangement is not to be construed as limiting the invention because other suitable arrangements of these and other components (not shown) are envisioned.

Medical ventilator 2 can include a controller 42 for receiving the flow signals from flow sensors 12 and 36, for receiving the pressure signal from pressure sensor 32, and for receiving the signal output by thermocouple TC corresponding to a temperature of bacteria filter 38. Controller 42 is responsive to these signals for controlling the operation of pressure generator 8 and flow control valves 10 and 34 in a manner known in the art.

Figure 2:
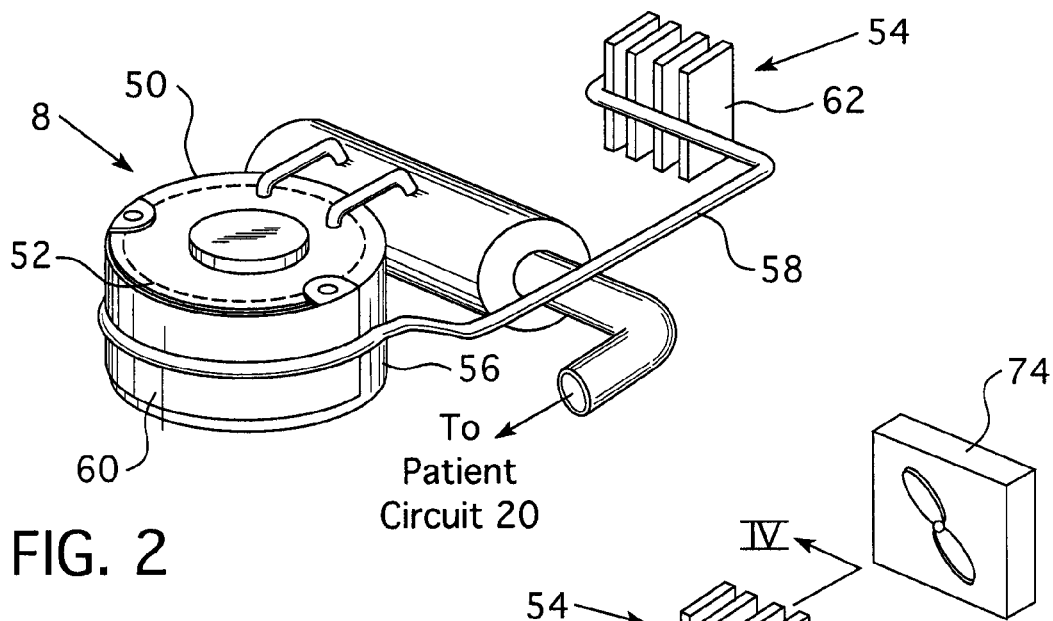
FIG. 2 is an isolated perspective view of the pressure generator, the heat pipe and the heat sink assembly of the medical ventilator shown in FIG. 1.

With reference to FIG. 2, and with continuing reference to FIG. 1, it is not uncommon during operation that pressure generator 8, especially a motor 50 of pressure generator 8, generates heat that undesirably raises a temperature of the pressurized gas delivered to patient P. More specifically, heat produced by operation of motor 50 driving a suitable pressure increasing means 52, shown in phantom in FIG. 2, increases a temperature of the pressurized gas output by pressure generator 8. This temperature increase is in addition to the temperature increase caused by the pressurization of the gas by pressure generator 8.

To avoid increasing the temperature of the pressurized gas to an undesirable level, a heat sink assembly 54 can be positioned in spaced relation to a housing 56 of pressure generator 8. Housing 56 can be the housing of motor 50 or can be a housing that encompasses motor 50 and pressuring increasing means 52 as shown in FIG. 2. Desirably, pressure increasing means 52 is a compressor, such as a blower, a piston, a bellows, a helical compressor, or a drag compressor.

Heat sink assembly 54 is desirably thermally conductive. In order to effectively transfer heat between housing 56 and heat sink assembly 54, a thermal conductor 58 is coupled between housing 56 and heat sink assembly 54. To enable thermal conductor 58 to effectively sink heat from housing 56, an evaporator plate 60 is coupled in thermal communication between housing 56 and a length of thermal conductor 58 adjacent housing 56.

Desirably, thermal conductor 58 is a heat pipe of the type commercially available from the Thermacore Division of Modine Manufacturing Company of 780 Eden Road, Lancaster, Pa. 17604. The basic operation of such a heat pipe is disclosed in, among other places, U.S. Pat. No. 4,951,740 to Peterson et al. which is incorporated herein by reference.

Heat sink assembly 54 can be of any conventional design. One such design includes a plurality of spaced heat dissipating elements 62 coupled in an appropriate manner to thermal conductor 58. In operation, heat produced in response to operation of pressure generator 8 is transferred to heat sink assembly 54 via thermal conductor 58. The transfer of heat to heat sink assembly 54 via thermal conductor 58 enables pressure generator 8 to pressurize gas without increasing the temperature of the pressurized gas to undesirable levels.

Figure 3:
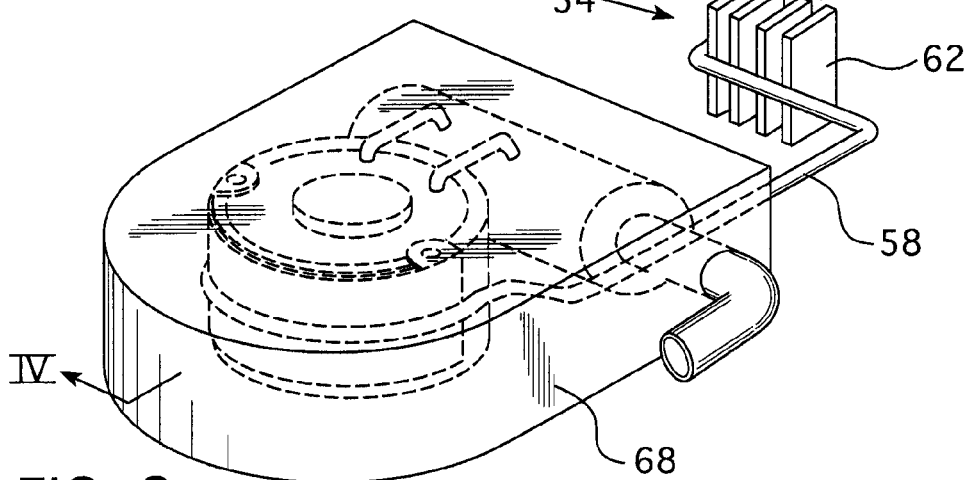
FIG. 3 is a perspective view of the pressure generator and heat pipe shown in FIG. 2 received in an enclosure along with a fan positioned adjacent the heat sink assembly for causing air to flow thereacross.
Figure 4:
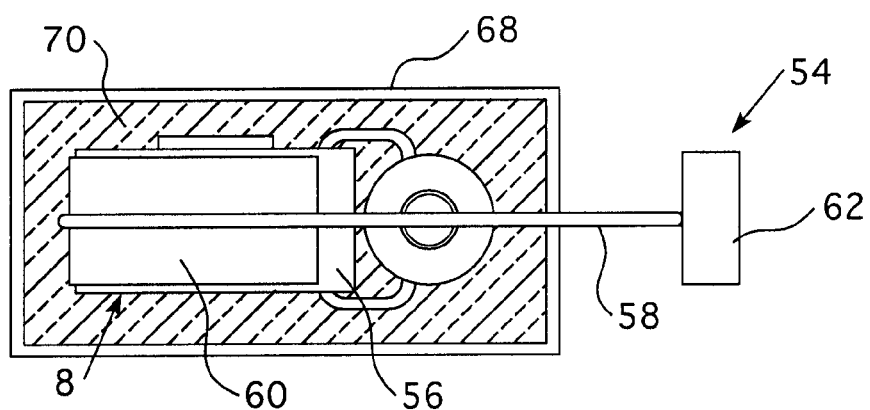
FIG. 4 is a cross-section taken along lines IV-IV in FIG. 3.

With reference to FIGS. 3 and 4, and with continuing reference to FIGS. 1 and 2, pressure generator 8, evaporator plate 60 and part of thermal conductor 58 are received inside of a housing 68 that includes a suitable composite foam 70 therein surrounding pressure generator 8, evaporator plate 60 and at least part of thermal conductor 58.

A fan 74 can be provided for causing ambient temperature air to flow across heat sink assembly 54 to remove heat therefrom. Fan 74 can either be controlled by controller 42, as shown in FIG. 1, or can be directly connected to a source of electrical power (not shown) that supplies power to fan 74 when medical ventilator 2 is turned on.

FIGS. 2-4 show the various components thereof in isolation. However, as would be appreciated by one of ordinary skill in the art, the components shown in these figures are connected as discussed above in connection with FIG. 1 and are received in a larger enclosure (not shown) which forms the outer shell of medical ventilator 2.

Figure 5:
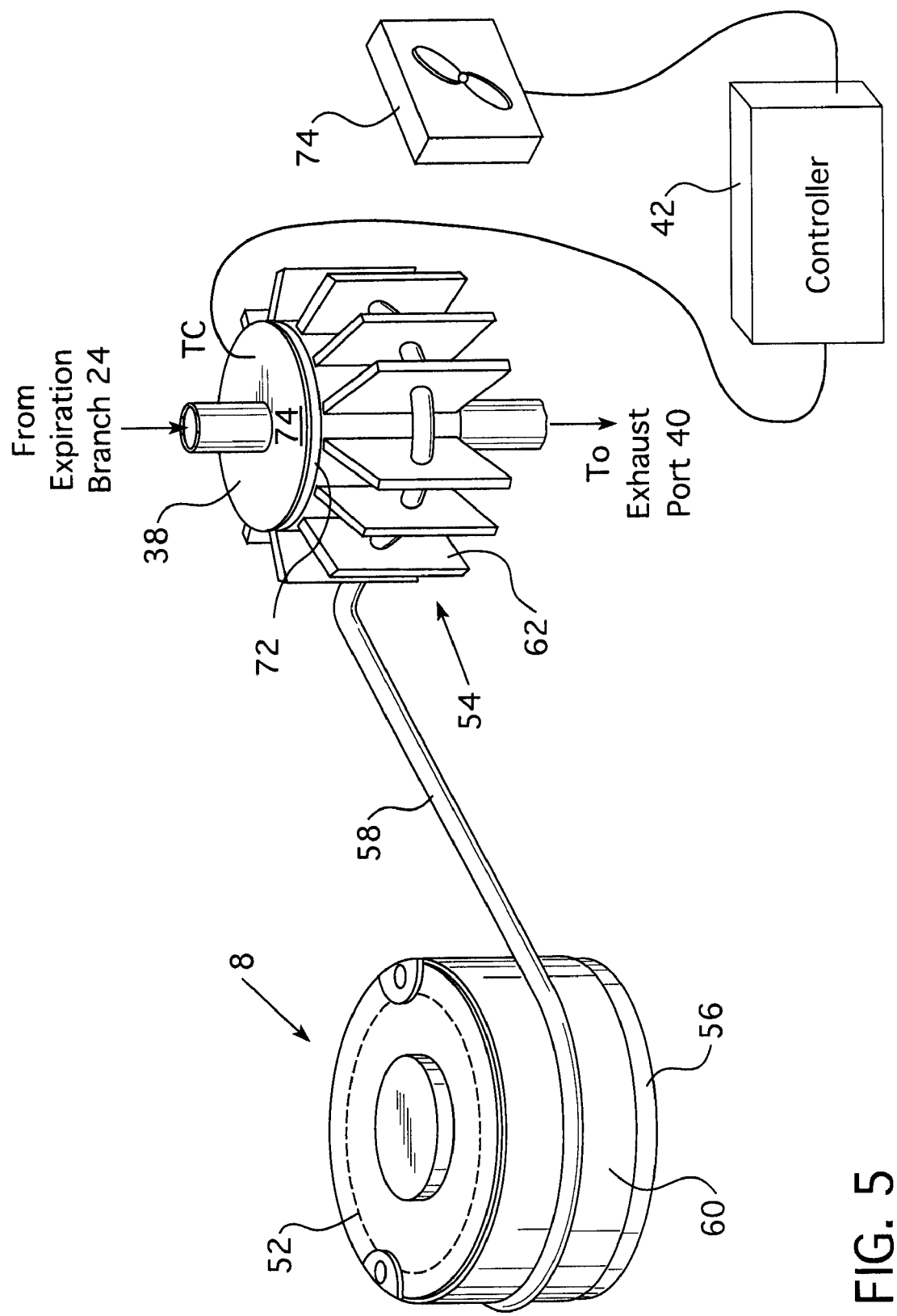
FIG. 5 is an isolated perspective view of the pressure generator, heat pipe, heat sink assembly, bacteria filter, controller and fan shown in FIG. 1.

With reference to FIG. 5, and with continuing reference to FIGS. 1-4, because bacteria filter 38 requires heating for the effective operation thereof, heat sink assembly 54 can be placed in contact with bacteria filter 38 thereby enabling bacteria filter 38 to be heated with heat produced by pressure generator 8. Desirably, heat sink assembly 54 includes an interface plate 72 between the body of bacteria filter 38 and heat dissipating element(s) 62, such as fins of heat sink assembly 54. Desirably, interface plate 72 has a surface that is arranged to contact a surface of bacteria filter 38.

Thermocouple TC detects the temperature of bacteria filter 38 and provides a corresponding signal to controller 42. Controller 42 analyzes this signal and causes fan 74 to turn on when the temperature of bacteria filter 38 exceeds a predetermined temperature. As discussed above, fan 74 is operative for causing ambient air to flow across heat sink assembly 54 to remove heat therefrom. Thus, heat produced by pressure generator 8 can be utilized to heat bacteria filter 38 to its effective operating temperature while controller 42 can selectively cause fan 74 to turn on to maintain the temperature of bacteria filter 38 within its effective operating temperature range.

As can be seen, the present invention enables heat produced by the operation of pressure generator 8 to be conveyed therefrom for dissipation by heat sink assembly 54. The use of a heat pipe as thermal conductor 58 enables the effective transfer of heat from pressure generator 8 to heat sink assembly 54 while avoiding the need for larger, bulkier thermal conductors 58 which may require for their accommodation a redesign of the housing of medical ventilator 2. In addition, the heat dissipated by heat sink assembly 54 can be advantageously utilized to heat bacteria filter 38 to a suitable operating temperature in excess of ambient temperature thereby avoiding the need to provide a separate heating means, such as a resistive heater, for heating bacteria filter 38 to its effective operating temperature range.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A medical ventilator comprising:
   a patient circuit having an inspiration branch and an expiration branch;
   a pressure generator operatively coupled to the inspiration branch, wherein during operation the pressure generator (a) increases a pressure of gas to be delivered to a patient via the inspiration branch of the patient circuit and (b) produces heat;
   first means requiring heating in excess of an ambient temperature for the effective operation thereof, wherein the first means is spaced from the pressure generator and coupled to the expiration branch such that exhaled gas from the patient is provided to the first means, and wherein the first means is physically separated from the pressure generator; and
   a thermal conductor coupled in thermal communication with the first means and the pressure generator so as to transfer at least part of heat produced by the pressure generator during the operation thereof to the first means, and wherein the thermal conductor is physically separated from the patient circuit.

2. The ventilator of claim 1, further including a thermally conductive heat sink coupled in thermal communication between the first means and the thermal conductor.

3. The ventilator of claim 2, further including a means for causing air to flow across the heat sink.

4. The ventilator of claim 1, wherein the thermal conductor is a heat pipe.

5. The ventilator of claim 1, wherein the pressure generator includes a motor for driving a compressor.

6. The ventilator of claim 5, wherein the compressor includes one of a blower, a piston, a bellows, a helical compressor and a drag compressor.

7. The ventilator of claim 1, further including an enclosure encasing the pressure generator and at least a part of the thermal conductor.

8. The ventilator of claim 7, further including an insulative material disposed in the enclosure.

9. A medical ventilator comprising:
- a patient circuit having an inspiration branch and an expiration branch;
- a pressure generator operatively coupled to the inspiration branch, wherein during operation the pressure generator (a) increases a pressure of gas to be delivered to a patient via the inspiration branch of the patient circuit and (b) produces heat;
- a heat sink coupled to the expiration branch and physically separated from the pressure generator; and
- a thermal conductor coupled in thermal communication with the pressure generator and the heat sink for transferring at least part of the heat produced by the pressure generator during the operation thereof to the heat sink, and wherein the thermal conductor is physically separated from the patient circuit.

10. The ventilator of claim 9, further including means for causing air to flow across the heat sink to remove at least part of the heat conducted to the heat sink by the thermal conductor.

11. The ventilator of claim 9, wherein the thermal conductor is a heat pipe.

12. The ventilator of claim 9, wherein the pressure generator includes a motor for driving a compressor.

13. The ventilator of claim 12, wherein the compressor includes one of a blower, a piston, a bellows, a helical compressor and a drag compressor.

14. The ventilator of claim 9, further including an enclosure encasing the pressure generator and at least part of the thermal conductor.

15. The ventilator of claim 14, further including an insulative material disposed in the enclosure.

16. A medical ventilator comprising:
- gas pressure increasing means for increasing a pressure of gas, wherein the gas pressure increasing means also produces heat during the operation thereof;
- means for conveying the pressurized gas from the gas pressure increasing means to a patient; and
- heat absorbing means for absorbing heat spaced apart and physically separated from the gas pressure increasing means;
- heat requiring means requiring heating in excess of an ambient temperature for the effective operation thereof, the heat requiring means coupled in thermal communication with the heat absorbing means;
- thermally conductive means coupled in thermal communication with the heat absorbing means and the pressure increasing means for conveying at least part of the heat produced by the gas pressure increasing means to the heat requiring means, and wherein the thermally conductive means is physically separated from the inspiratory limb of the medical ventilator; and
- means for conveying gas exhaled by the patient to the heat requiring means.

* * * * *